United States Patent [19]

Boone

[11] Patent Number: 4,864,852
[45] Date of Patent: Sep. 12, 1989

[54] METHOD AND APPARATUS FOR MEASURING THE CUT RESISTANCE OF FLEXIBLE MATERIALS

[75] Inventor: Mark B. Boone, Richmond, Va.

[73] Assignee: Allied-Signal Inc., Morris Township, Morris County, N.J.

[21] Appl. No.: 223,596

[22] Filed: Jul. 25, 1988

[51] Int. Cl.$^4$ ............................................. G01N 3/56
[52] U.S. Cl. ........................................ 73/159; 73/7; 73/81; 73/839; 73/432.1
[58] Field of Search ...................... 73/7, 839, 159, 78, 73/81, 432.1

[56] References Cited

U.S. PATENT DOCUMENTS

| | | | |
|---|---|---|---|
| 2,687,641 | 8/1954 | Stout | 73/159 |
| 3,026,726 | 3/1962 | Reading | 73/159 |
| 3,641,807 | 2/1972 | Brooks | 73/7 |
| 3,971,245 | 7/1976 | Crafford et al. | 73/7 |

Primary Examiner—William A. Cuchlinski, Jr.
Assistant Examiner—Diego F. F. Gutierrez
Attorney, Agent, or Firm—Richard A. Anderson

[57] ABSTRACT

Method and apparatus for measuring the cut resistance of flexible materials, such as films, fabrics, felts and papers. A flexible material is wrapped around a mandrel that is rotated at a predetermined speed. A cam attached to the rotating mandrel allows a cutting edge, such as a razor blade, to repeatedly fall on the material covering the mandrel. The cutting edge repeatedly contacts the material, in the same location and with the same predetermined force, until the cutting edge penetrates the material and makes electrical contact with the mandrel. When edge-to-mandrel contact is made, the rotation of the mandrel is automatically stopped. The number of rotations (i.e. cutting cycles) required to penetrate the material is noted and used as a measure of the relative cut resistance of the material.

14 Claims, 2 Drawing Sheets

METHOD AND APPARATUS FOR MEASURING THE CUT RESISTANCE OF FLEXIBLE MATERIALS

BACKGROUND OF THE INVENTION

This invention relates to a method and apparatus for measuring cut resistance of flexible materials.

This invention was developed due to the need for a simple and reliable test to measure the cut resistance of fabrics used to make protective clothing. Manufacturers and users of protective gloves and other garments previously had no widely accepted means of evaluating the cut protection of such products. Previous cut tests were relatively crude and often very subjective. In some cases the test conditions did not closely simulate the conditions under which the wearer of the protective clothing would actually be cut.

Features of a cut test that are generally desirable include the following. The sample should be tested under conditions similar to those that would be present when the item is in normal use. For example, if a garment is loosely worn, it would not be desirable to test that garment fabric under conditions where it is highly stretched or under high tension. The sharpness of the cutting blade should be the same for each sample tested, since it is well known that the cut resistance of any material is related to the sharpness of the blade that is cutting it. The test conditions should be able to be varied widely so that the speed and force of the cut used during the test can closely simulate the wide variety of cutting conditions that could be encountered in the actual use of a product. The test should be automated as much as practical so that the results are repeatable and not highly subjective. The test should be capable of testing relatively small samples; for example, a fabric only a few inches square. The test should allow a single sample, even a small sample, to be tested several times for more accurate results. The test equipment should be as small and lightweight as practical. A portable tester that could be easily carried by one person would be very desirable.

It is the primary objective of this invention to provide a means of reliably measuring the cut resistance of materials used in the manufacturing of cut protective garments. The invention has been found useful for measuring the cut resistance of almost any flexible article, including films, woven fabrics, nonwoven fabrics, knitted fabrics, felts and papers.

SUMMARY OF THE INVENTION

The present invention provides a simple means of cutting flexible materials in a controlled manner so that the relative cut resistance of the materials can be measured. In the practice of this invention a flexible material, such as a film or fabric, is wrapped around an electrically conductive mandrel. An electrically conductive cutting edge, such as a razor blade, is mounted on a pivoting arm that is perpendicular to the mandrel. The vertical position of the cutting edge on the arm is controlled by a cam that is attached to the mandrel. The cam is shaped so that the arm is allowed to drop onto the mandrel at a predetermined point in the rotation cycle of the cam. The mandrel and cam are rotated at a predetermined speed so that the arm is repeatedly allowed to fall on the mandrel. As the arm falls, the cutting edge attached to it contacts the material wrapped around the mandrel. The mandrel will continue to rotate and the blade will repeatedly cut the material in the same location until the cutting edge penetrates the material and touches the mandrel. When the edge-to-mandrel contact is made, which results in electrical contact being made, the rotation of the mandrel is automatically stopped. The number of rotations, and therefore number of cuts, required to penetrate the material is a measure of its cut resistance. For a given set of test conditions, a more cut resistant material will require a larger number of cuts before it is penetrted.

The present invention can also be used to measure the abrasion resistance of a material. This is done by replacing the cutting edge with an abrasive surface. If the abrasive surface is electrically conductive, the tester will automatically stop upon penetration of the sample.

More specifically this invention is a method for determining cut resistance of a flexible material, comprising mounting a sample of the material on a surface, moving the surface in a repetitive motion so that the sample will repeatedly return to precisely the same position, contacting the sample on the surface with a sharp or abrasive edge repeatedly, with the sample moving and in the same precise position so that the same portion of the sample is contacted each time, and counting the number of the repeated contacts of the edge with the sample required to cut through the sample. The repetitive motion can be either rotational or reciprocating. If reciprocating, the preferred motion is a cycle of one rotation back and forth rather than reciprocation in the direction of the axis of the mandrel.

The preferred counting step is achieved by means for counting the repetitive motion, said counting being stopped by completion of an electrical circuit when the edge contacts the surface. It is also preferred to load the edge with a weight so that the force of the edge contact with the material samples remains substantially constant for each repeated contact.

This invention is also an apparatus for measuring cut resistance of flexible materials comprising means for mounting a sample of the material, means for moving the sample in a repetitive motion so that the sample will repeatedly return to precisely the same position, means for repeatedly contacting the sample with a sharp or abrasive edge while the sample is moving, and in the same precise position at each contact, and means for counting the number of contacts required to cut through the sample. The preferred mounting means is a mandrel. The preferred means for moving the mandrel is a motor attached to the mandrel so as to rotate or reciprocate the mandrel. The preferred means for repeatedly contacting the edge with the sample is the edge being mounted in a pivoting arm which is proximate to the moving sample so that the edge can repeatedly contact the sample by pivoting the arm toward and then away from the sample. It is preferred to control the pivoting of the arm by a rotating cam. It is preferred that the arm be mounted above the sample and weights be placed on the arm. The preferred counting means is means to count the cycles of repetitive motion with the counting means being stopped by a completion of an electrical circuit when the edge breaks through the sample and touches the mandrel.

DETAILED DESCRIPTION

Figure 1:
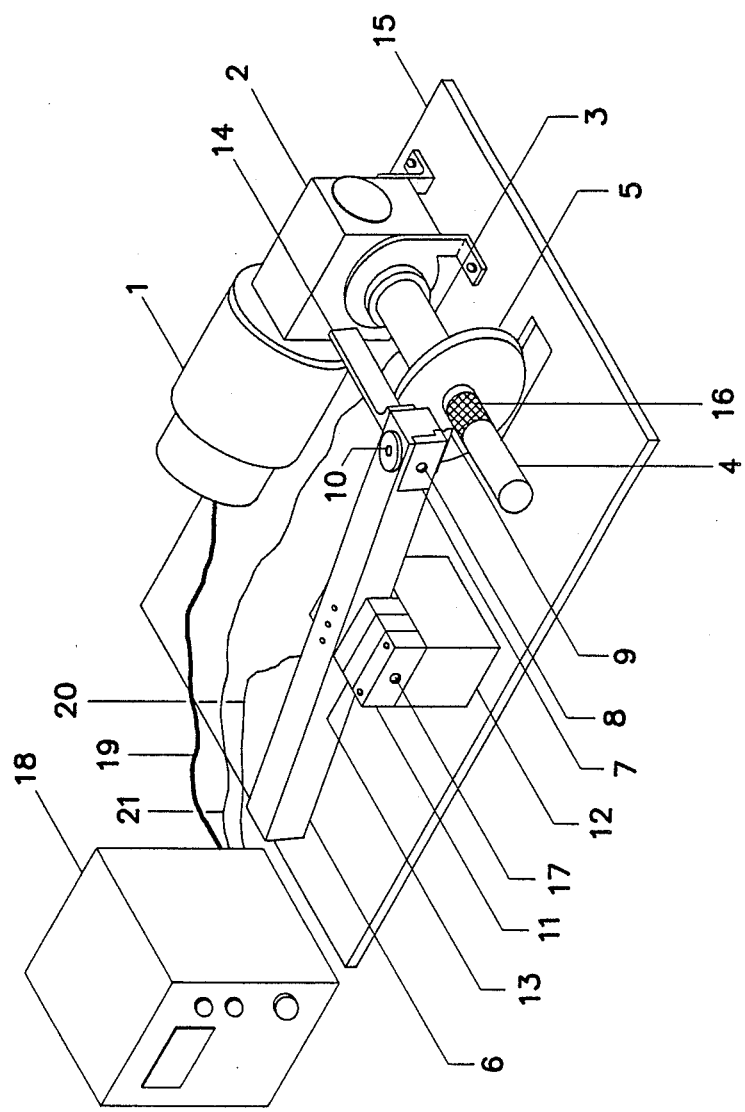
FIG. 1 is an overall-view of the testing machine.

As shown in FIG. 1, the cutting arm 6 is held perpendicular to the centerline of the rotating mandrel 4. As a result, the cutting blade 9, which is held on the arm by clam 7 and screw 8, will make a straight, slicing cut in any material placed on the rotating mandrel. The mandrel is rotated under the power of motor 1 and is connected to the motor by a gearbox 2 and shaft coupling 3. A cam 5, which is attached to the rotating mandrel, controls the position of the cutting arm through a lever 14 which is rigidly attached to the cutting arm. The shape of the cam determines at what point the cutting blade will be lowered so as to contact the sample being tested, and determines when the blade will be lifted away from the sample. The sample would be placed over the mandrel terminating at knurled region 16.

The amount of energy applied to the sample during each cutting stroke is controlled by the amount of weight 10 applied to the cutting arm and the height of the drop that the cam 5 allows. Changing the arm weight and the diameter of the cam also changes the vertical velocity with which the blade impacts the sample. The speed at which the sample is cut, which is the horizontal velocity at the point of impact, is controlled by the speed of the drive motor.

The cutting arm is supported by a shaft 17 which rides in electrically insulating bearing blocks 11 that are placed on both sides of the arm. The bearing blocks are attached to a support 12 that holds the arm at the proper height above the base plate 15. The spacing between bearings is such that the arm is free to move laterally. Removable spacers 13 are used to center the arm in the desired location. This design allows the arm to be moved in discrete steps so that multiple tests can be performed on one sample, with each cut test being made at a different location along the length of the mandrel. FIG. 1 shows an example where a sample would be cut on the cam side of the mandrel. Moving the arm laterally and placing the spacers on the other side of the arm would result in a cut near the open end of the mandrel.

In FIG. 1 is shown a typical electrical enclosure 18 that could be used as part of this invention. The power for the variable-speed motor is carried through a cable 19. The speed of the motor can be adjusted with a dial on the front of the enclosure. Switches are located on the enclosure to start and stop the motor. A digital display on the enclosure indicates the number of revolutions of the mandrel between the time the motor was started and stopped. The rotations are detected by a sensor, such as a microswitch, located near the shaft coupling 3. The sensor is connected to the enclosure by a wire 21. The motor will automatically be stopped whenever the metal blade 9 contacts the electrically conductive mandrel 4. When the blade contacts the mandrel an electrical contact is made. This electrical signal is carried to the enclosure by wire 20. Electrical circuitry in the enclosure removes power from the motor when the signal is received from a blade-to-mandrel contact. Generally, the cutting arm is metallic so that the signal wire 20 is connected to the arm rather than directly to the blade.

Figure 2:
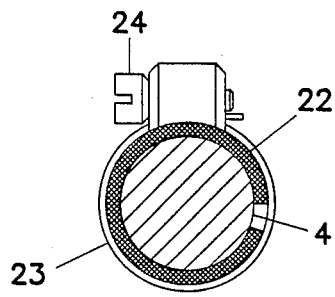
FIG. 2 is a section-view of a mandrel that has a fabric sample wrapped around it, with the sample being secured to the mandrel by a circular clamp.

FIG. 2 shows an example of a fabric sample 22 wrapped around the tester mandrel 4. The fabric is held on the mandrel by a band-clamp 23 that is tightened by a screw 24. The clamp is placed over the mandrel in the knurled region 16 shown in FIG. 1. A sample may also be attached to the mandrel with pressure sensitive tape or by other means.

Figure 3:
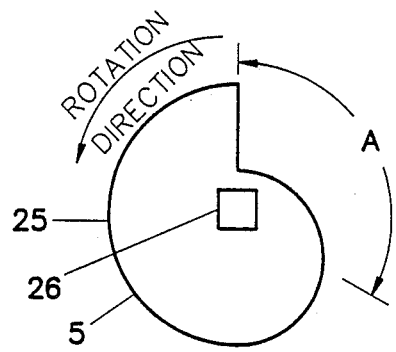
FIG. 3 is a view of a typical cam that would be used to abruptly drop the cutting arm in a predetermined location during testing.

FIG. 3 is a view of a typical cam 5 that would be used to drop the cutting arm in a predetermined location on the mandrel. The arm lever rides on the outer surface 25 of the cam. The inner cutout 26 slides over and engages the mandrel shaft so that the cam turns at the same speed as the mandrel. Since the cam and mandrel rotate at the same speed, the blade will fall in the same location with each rotation of the mandrel. The angle A over which the arm is free to drop and allow the blade to contact the mandrel is shown.

Figure 4:
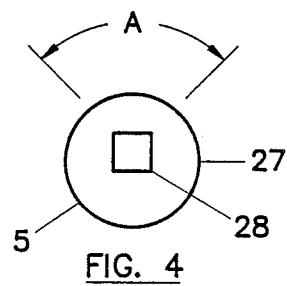
FIG. 4 is a view of a typical cam that would be used to gently lower the cutting arm onto the sample during testing.

FIG. 4 shows a cam 5 design that allows the blade to be gently lowered onto the mandrel, due to the gradual change in radius of its outer surface 27. The cam is attached to the mandrel shaft through cutout 28. The angle A through which blade-to-mandrel contact can be made is shown.

Normal operation of the equipment shown in FIG. 1 would involve the following procedures. A mandrel of the appropriate diameter would be chosen. If the test sample is a finger cut from a glove, for instance, the mandrel should be a diameter that allows the finger to easily slide on the mandrel, so that the sample is not overly stretched when mounted. The sample is mounted on the mandrel and a cam, with the proper shape, is slipped on the mandrel shaft. When the sample and cam are placed on the mandrel, their relative position to each other will determine the location at which the blade will contact the sample. The mandrel assembly is then mounted in the gearbox coupling. A new blade is mounted in the cutting arm and the desired cutting weight is added to the arm. The arm should be balanced before the weights are added so that the cutting force is due only to the added weights and not the weight of the arm itself. Typically about 10 to 1,000 g are used to weight the arm, preferably about 45 to 200 g.

Once the sample is mounted and a new blade has been placed in the arm, the counter used to record the number of mandrel rotations is reset to zero. The dial used to set motor speed is set to the desired value in the range of 1 to 250 rpm, preferably 10 to 100 rpm. The start switch is activated to start the cut test. Once the test is started the sample will be repeatedly cut in the same location until the blade contacts the mandrel. When blade-to-mandrel contact is made the mandrel will stop turning. The number of cuts (i.e., rotations) required for the blade to penetrate the sample can then be noted. This number represents a relative level of cut resistance for the test conditions selected.

The surface hardness of the mandrel can be changed to simulate surfaces which would be used to support a cut resistant material in actual use. When the counter is stopped by electrical contact, the major requirement is that the outer surface of the mandrel be electrically conductive. For example, an electrically conductive form or film can be wrapped around a metal mandrel to provide a softer backing for the material being cut tested. However, other means to stop the counter could be used.

This invention has been found particularly useful for measuring the cut resistance of protective gloves. It is a simple procedure to cut a finger from a glove and clamp it on the tester's mandrel. In this way, the cut resistance of any glove can be tested. This allows glove users the ability to quickly compare the cut resistance of any commercially available protective glove. In a similar fashion, this invention can be used by glove manufacturers to determine if changes that are made during the manufacturing of a glove result in a change in the cut resistance of that glove.

An advantage of the present invention over previous cutting tests is that it can closely simulate the conditions of a glove finger being worn during normal use. When the proper size mandrel is used, the glove finger is under little tension and is free to move slightly on the mandrel. As a result, when the cutting edge is dropped on the glove finger the finger can deform slightly. A glove worn on the hand is under similar conditions in that it is not normally highly stretched, but rather is somewhat flexible on the hand.

The cam used to lift the cutting arm is shaped so that the arm is repeatedly raised and lowered as the mandrel rotates. This feature is an advantage over previous tests due to the fact that only selected parts of the sample are actually cut. Parts of the sample that are placed on the mandrel in the area where the cam lifts the arm will not be exposed to contact with the cutting edge. This can be used to an advantage. A seam or fold in the sample material can be placed in the area where cutting does not occur. In this manner only the flat surfaces of the sample will be cut. Also, if the sample is not large enough to cover the complete circumference of the mandrel, the gap between the ends of the sample can be placed in the area of the mandrel where no cutting occurs.

It should be noted that the mandrel can be made to various shapes if desired. For example, the mandrel could be made the shape of a human finger in order to more closely simulate the cutting of a glove finger while it is being worn.

Since the cut test is ended when the cutting edge makes electrical contact with the manrel, testing of materials that are themselves electrically conductive requires special consideration. In most cases conductive materials can be successfully tested if a thin layer of insulating material is placed between the sample and the mandrel. For example, the mandrel can be wrapped with a thin piece of polyethylene film before the sample is mounted on the mandrel. Thin polythylene films will generally not add to the number of cuts required to contact the mandrel since such films are so easily cut.

It is clear to the skilled artisan that mechanical equivalents to the above-described apparatus means could also be used in this invention. For example, rather than a cam for moving the pivoting arm, the arm could be mounted eccentrically on a wheel or disc, either linked or timed to coincide with the rotating mandrel. The arm could also be actuated by a solenoid, electrically timed to coincide with the same portion of the sample. The arm could be forced into the sample by means of a spring or magnetic force. Many other such equivalent means are readily apparent.

By edge herein is meant either a sharp cutting narrow surface or an abrasive relatively more broad surface for abrading the sample.

We claim:

1. A method for determining cut resistance of a flexible material comprising
   mounting a sample of said material on an electrically conductive surface,
   moving said surface in a repetitive motion so that said sample will repeatedly return to precisely the same position,
   contacting said sample on said surface with an electrically conductive edge repeatedly with said sample moving and returning to said same precise position so that the same portion of said sample is contacted each time, and counting the number of said repeated contacts of said edge with said sample required to cut through said sample, and said counting is achieved by means of counting said repetitive motion, said counting being stopped by completion of an electrical circuit when said electrically conductive edge contacts said electrically conductive mounting surface.

2. The method of claim 1 wherein said repetitive motion is rotational.

3. The method of claim 1 wherein said repetitive motion is reciprocating.

4. The method of claim 1 wherein said edge is loaded with a weight so that the force of the edge contact with said sample material remains substantially constant for each repeated contact.

5. The method of claim 1 wherein the edge is sharp.

6. The method of claim 1 wherein the edge is abrasive.

7. An apparatus for measuring cut resistance of flexible material comprising
   means for mounting a sample of said material on an electrically conductive surface
   means for moving said sample in a repetitive motion so that said sample will repeatedly return to precisely the same position,
   means for repeatedly contacting said sample with an electrically conductive edge, while said sample is moving, and in the same precise position at each contact, and said means for repeatedly contacting said edge with said sample is said edge being mounted in a pivoting arm which is proximate to said moving sample, so that said edge can repeatedly contact said sample by pivoting said arm toward and then away from said sample, and
   means for counting the number of said contacts required to cut through said sample, said means being means to count the cycles of repetitive motion with said counting means being stopped by completion of an electrical circuit when said edge breaks through said sample and contacts said electrically conductive mounting surface.

8. The apparatus of claim 7 wherein said mounting means is a mandrel.

9. The apparatus of claim 8 wherein said means for moving said mandrel is a motor attached to said mandrel so as to rotate said mandrel.

10. The apparatus of claim 8 wherein said means for moving said mandrel is a motor attached to said mandrel so as to reciprocate said mandrel.

11. The apparatus of claim 7 wherein the edge is sharp.

12. The apparatus of claim 7 wherein the edge is abrasive.

13. The apparatus of claim 7 wherein said pivoting is controlled by a rotating cam.

14. The apparatus of claim 7 wherein said arm is mounted above said sample and weights are placed on said arm to control a cutting force.

* * * * *